(12) United States Patent
Miller (10) Patent No.: US 6,920,777 B1
(45) Date of Patent: Jul. 26, 2005

(54) INTAKE CROSS-SHEETS FOR GAS CHROMATOGRAPHIC OVEN

(75) Inventor: Sammye Miller, New Castle, DE (US)

(73) Assignee: Agilent Technologies, Inc., Palo Alto, CA (US)

( * ) Notice: Subject to any disclaimer, the term of this patent is extended or adjusted under 35 U.S.C. 154(b) by 1 day.

(21) Appl. No.: 10/768,165

(22) Filed: Feb. 2, 2004

(51) Int. Cl.[7] ............................................. G01N 30/02
(52) U.S. Cl. ...................... 73/23.25; 73/23.35; 96/107; 96/127; 422/89
(58) Field of Search ........................... 73/23.25, 23.26, 73/23.35; 96/127, 107, 101; 55/342.1; 219/391; 422/89

(56) References Cited

U.S. PATENT DOCUMENTS

| | | | |
|---|---|---|---|
| 4,461,950 A | | 7/1984 | Curless et al. |
| 4,757,800 A | * | 7/1988 | Shei et al. .................. 126/21 A |
| 5,683,240 A | * | 11/1997 | Smith et al. .................. 432/59 |
| 5,830,262 A | * | 11/1998 | Marchini et al. ............. 96/105 |
| 6,248,158 B1 | * | 6/2001 | Abdel-Rahman et al. ...... 96/101 |
| 6,623,352 B2 | * | 9/2003 | Illingworth ................. 454/189 |

* cited by examiner

Primary Examiner—Michael Cygan (57) ABSTRACT

An apparatus, system and method reduce the cool down time of GC ovens by supplying larger volumes of air through oven intake ducts. The system and method provide intake cross-sheets in an oven intake duct to reduce airflow spin, increasing the flow rate of fresh air into the GC oven and reducing the overall cool-down time of the GC oven. In addition, because the improved airflow allows the oven wall temperature to quickly match the oven air temperature, the noise in the temperature signal may be reduced. As a result, the GC oven can reach an equilibrium "ready" state faster. Furthermore, the utilization of the cross-sheets may allow for flexibility in the design of a fast GC oven—specifically in the location and shape of the intake duct—without loss of performance. This flexibility may become increasingly significant as GC ovens continue on the trend of becoming smaller and faster.

19 Claims, 6 Drawing Sheets

INTAKE CROSS-SHEETS FOR GAS CHROMATOGRAPHIC OVEN

TECHNICAL FIELD

The technical field relates to a gas chromatographic oven, and, in particular, to oven cooling efficiency.

BACKGROUND

Gas chromatography (GC) is a physical method for the separation, identification, and quantification of chemical compounds. A sample mixture is injected into a flowing neutral carrier stream and the combination flows through a tube or chromatographic column. The inner surface of the column is coated or packed with a stationary phase. As the sample mixture and carrier stream flow through the column, the components within the mixture are retained by the stationary phase to varying degrees depending on the relative volatility of the individual components and on their respective affinities for the stationary phase. Different chemical compounds are retained for different times by the stationary phase. When the individual mixture components are released into the carrier stream by the stationary phase, the components are swept towards the column outlet to be detected and measured by a detector. The specific compounds in the components of the mixture can be identified and their relative concentrations determined by measuring peak retention times and peak areas, respectively.

A current trend in chromatography is towards improving sample cycle time to increase customer throughput. Cycle time includes sample injection time, oven heating time, sample separation time, and oven cooling or equilibration time. To decrease sample residence time, ovens are increasingly becoming more powerful (higher wattage coils) and smaller (lower thermal mass). As the size of the oven shrinks, often the ductwork for the oven's intake and exhaust becomes more complex in order to fit in smaller places or to be located more remotely from the oven.

A geometry that is utilized in small and fast GC ovens includes one or more axial boxer intake fans connected to an intake duct of convergent geometry. The intake fans supply fresh air to the GC oven through the converging intake duct. The use of a converging intake duct allows larger intake fans located remotely from a small oven to be used during cool-down. However, further improvements can be made to this system to cool the oven more quickly.

SUMMARY

An oven intake for a gas chromatographic (GC) oven includes an intake duct having a convergent geometry to accommodate a small oven. The intake duct has one or more intake fans that supply airflow to the GC oven. The airflow originates from the one or more intake fans and flows through the intake duct into the GC oven. The oven intake further includes one or more cross-sheets positioned inside the intake duct parallel to a direction of the airflow flowing into the GC oven. The one or more cross-sheets reduce spin of the airflow originating from the one or more intake fans and guide the airflow through the intake duct into the GC oven.

A system for providing intake cross-sheets for a GC oven includes an intake duct having a convergent section to accommodate the GC oven located at one end of the intake duct. The system further includes one or more intake fans located remotely from the GC oven at an opposite end of the intake duct. The one or more intake fans supply airflow to the GC oven. The system further includes one or more cross-sheets positioned inside the intake duct parallel to a direction of the airflow flowing into the GC oven. The one or more cross-sheets reduce spin of the airflow originating from the one or more intake fans and reduce frictional losses of the airflow flowing into the GC oven.

A method for cooling an oven includes providing one or more cross-sheets inside an intake duct parallel to a direction of airflow flowing into the oven. The intake duct has a convergent geometry to accommodate the oven and has one or more intake fans located remotely from the oven. The one or more intake fans supply airflow for the oven. The utilization of the one or more cross-sheets reduces spin of the airflow originating from the one or more intake fans and reduces a cool-down time of the oven.

DESCRIPTION OF THE DRAWINGS

The preferred embodiments of a system and method for providing intake cross-sheets for a gas chromatographic (GC) oven will be described in detail with reference to the following figures, in which like numerals refer to like elements, and wherein.

DETAILED DESCRIPTION

Current small and fast gas chromatographic (GC) ovens may use a converging intake duct to connect remotely located larger intake fans to a small oven. However, a converging geometry downstream of an axial flow fan generally sustains airflow spin induced by the axial flow fan that can lead to significant frictional losses. This effect, in the specific case of conical geometry, is discussed in Bleier, Frank, *Fan Handbook: Selection, Application, and Design*, McGraw-Hill, 1998 (pp 1.09–1.11), but may be extended to include all geometry of convergent shape. The induced friction greatly reduces the speed of the airflow and the volume of fresh air flowing into the oven from the intake fans.

An apparatus, system and method reduce the cool down time of GC ovens by supplying larger volumes of air through oven intake ducts. The system and method provide intake cross-sheets in an oven intake duct to disrupt and reduce airflow spin, increasing the flow rate of fresh air into the GC oven and reducing the overall cool-down time of the GC oven. In addition, because the improved airflow allows the oven wall temperature to quickly match the oven air temperature, the noise in the temperature signal may be reduced.

As a result, the GC oven can reach an equilibrium "ready" state faster. Furthermore, the utilization of the cross-sheets may allow for flexibility in the design of a fast GC oven—specifically in the location and shape of the intake duct—without loss of performance. This flexibility may become increasingly significant as GC ovens continue on the trend of becoming smaller and faster.

Figure 1:
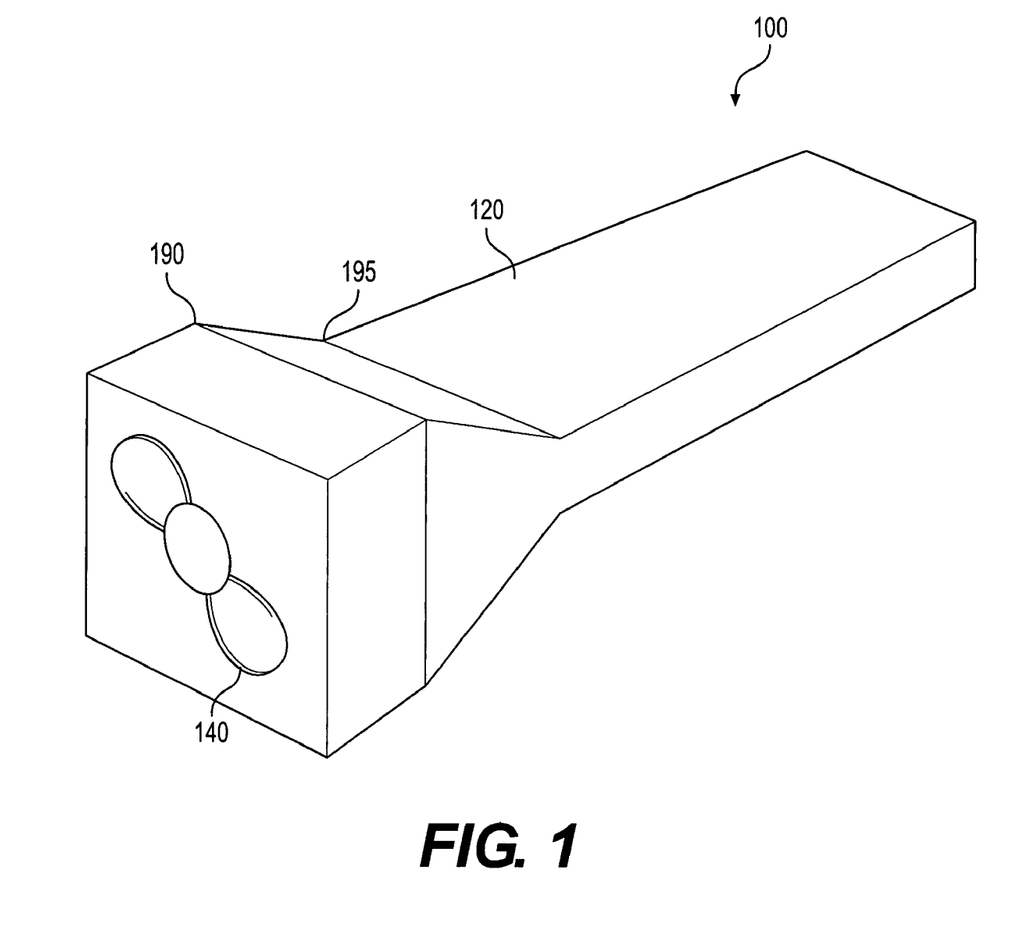
FIG. 1 illustrates an exemplary oven intake with a converging intake duct and an intake fan.

FIG. 1 illustrates an exemplary oven intake 100 with a converging intake duct 120 and an intake fan 140 located upstream at one end of the converging intake duct 120. The intake fan 140 may be an axial boxer fan. The intake fan 140 supplies fresh air to a GC oven (not shown) located remotely from the intake fan 140 at an opposite end of the converging intake duct 120. As shown in FIG. 1, the section of the intake duct 120 that is connected to the intake fan 140 has an approximately square cross-section 190. The intake duct 120 then converges to a rectangular cross-section 195 extending to the GC oven. As an example, an intake duct on an Agilent 6850GC oven is a duct of approximately 92 mm square cross-section (to accommodate a 92 mm boxer fan), that converges to a rectangle of 35 mm×92 mm cross-section (to fit behind the keyboard and display of a GC). The intake duct 120 may or may not have a conical shape.

Figure 2:
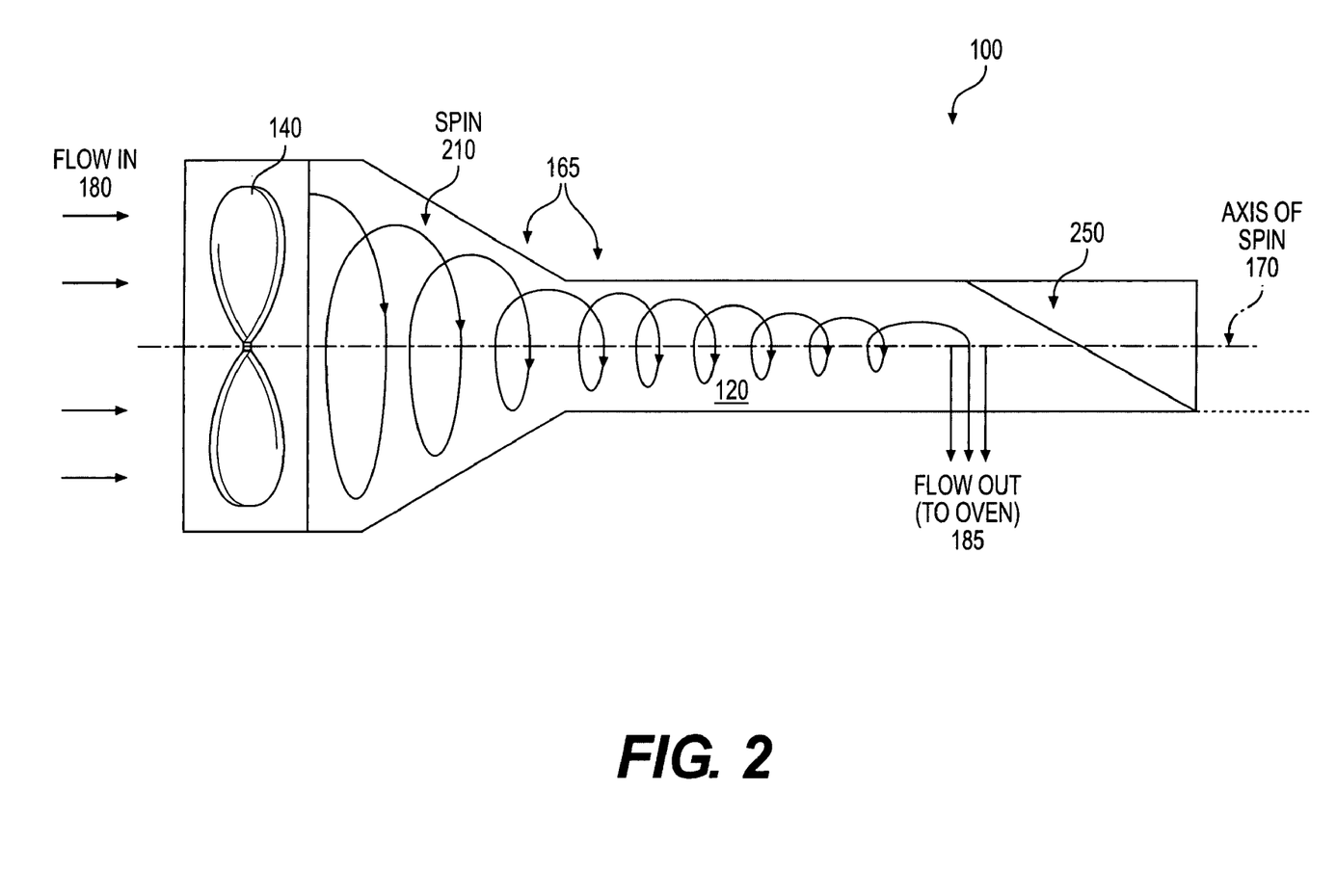
FIG. 2 illustrates a cutaway side view of the exemplary oven intake of FIG. 1 without cross-sheets showing the potential tendency for airflow spin.

FIG. 2 illustrates a cutaway side view of the exemplary oven intake 100 without cross-sheets showing the potential tendency for airflow spin 210. The intake duct 120 is shown with a convergent geometry 165. The intake fan 140 supplies airflow in the direction 180. The airflow flows through the converging intake duct 120 and into the GC oven in the direction 185. An intake flap 250 directs the airflow direction 185. Because the intake duct 120 has a non-uniform converging cross-section, the spin 210 induced by the axial intake fan 140 about an axis 170 may be sustained through the length of the intake duct 120. Airflow spin 210 may originate from a source other than the intake fan 140. The spin 210 may increase the effective distance the airflow travels, which in turn increases the frictional losses the airflow experiences due to interaction with the intake duct wall. This increased friction decreases the airflow flowing into the GC oven. To increase the velocity and volume of the airflow flowing into the GC oven, one or more cross-sheets 110 (shown in FIG. 3B) may be added to the intake duct 120 to reduce the airflow spin 210.

Figure 3A:
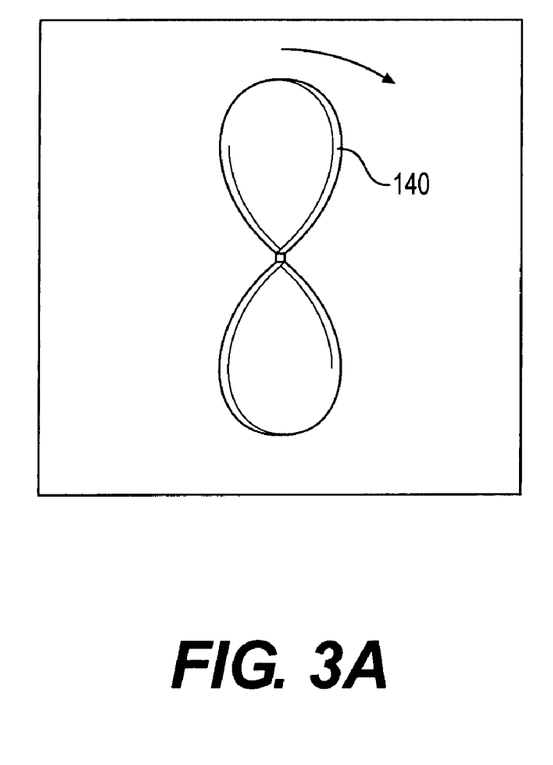
FIG. 3A illustrates a front view of the exemplary oven intake of FIG. 1 with the intake fan.
Figure 3B:
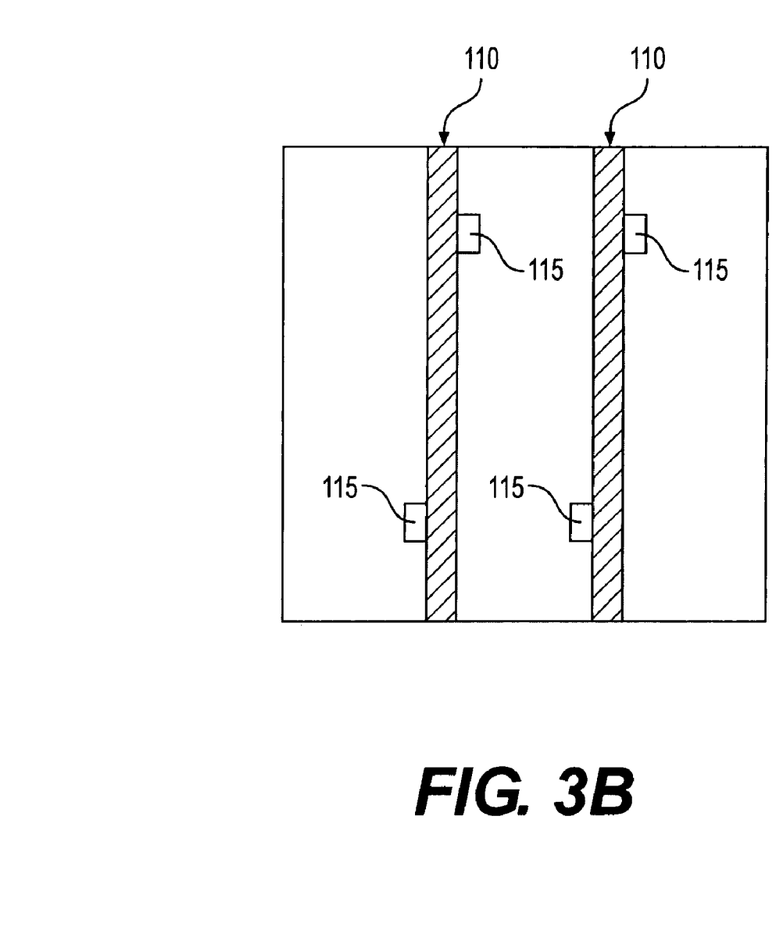
FIG. 3B illustrates another front view of the exemplary oven intake of FIG. 1 without the intake fan.

FIG. 3A illustrates a front view of the exemplary oven intake 100 with, the intake fan 140. FIG. 3B illustrates another front view of the exemplary oven intake 100 without the intake fan 140. Two cross-sheets 110 are shown in FIG. 3B. The cross-sheets 110 are located inside the intake duct 120 near the intake fan 140, such as 2 cm from the fan 140, and parallel to the direction of the airflow. The cross-sheets 110 shown here are trapezoidal in shape, with bases slightly undersized from 35 mm and 92 mm, to approximate the convergent section of the oven intake 100. However, other shapes and sizes of cross-sheets may be employed. The cross-sheets 110 may be secured to the intake duct wall by riveting metal tabs 115. If only one cross-sheet is used, the cross-sheet may be placed off-centered, for example, at one-third of the width of the intake duct 120 or one-third the diameter of the intake fan 140, to disrupt the spin 210. Additional cross-sheets may be used. For example, additional cross-sheets may be added alongside the cross-sheets 110 shown. One, two, three or more may be added. Also, cross-sheets may be added orthogonal to or at right angles to the cross-sheets 110 shown. A preferred embodiment is two cross-sheets placed in an "=" configuration at one-third and two-thirds of the width of the intake duct 120 or intake fan 140 diameter. Other arrangements of cross-sheets are possible with the same beneficial effect.

Figure 4:
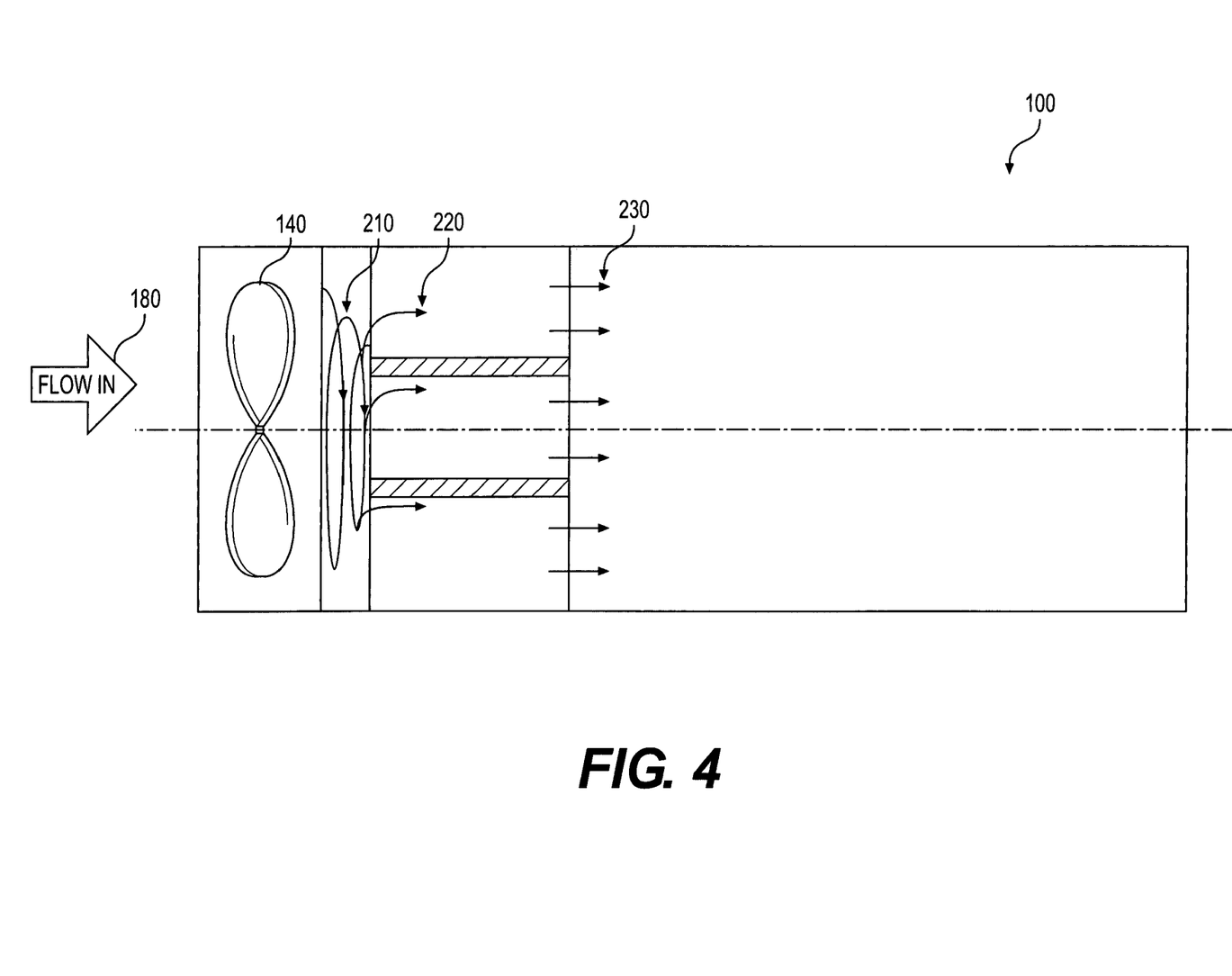
FIG. 4 illustrates a cutaway top view of the exemplary oven intake of FIG. 1 showing the location of cross-sheets inside the intake duct.

FIG. 4 illustrates a cutaway top view of the exemplary oven intake 100 showing the location of the cross-sheets 110 inside the intake duct 120. The intake fan 140 supplies airflow in the direction 180. The airflow flows through the converging intake duct 120 into the GC oven. As noted above, the intake fan 140 may induce airflow spin 210 about an axis 170. The utilization of the cross-sheets 110 disrupts 220 the tendency for the airflow to maintain spin 210 so that the airflow is guided 230 through the intake duct 120 to reach the GC oven. As a result, the frictional losses may be reduced because the distance over which any piece of fluid interacts with the intake duct wall is reduced. The reduced frictional losses may lead to increased airflow speed and consequently more fresh air flowing into the GC oven during cool-down. The cross-sheets 110 preferably are located close to the intake fan 140 to guide the airflow as soon as possible, such as 2 cm from the intake fan 140.

Figure 5:
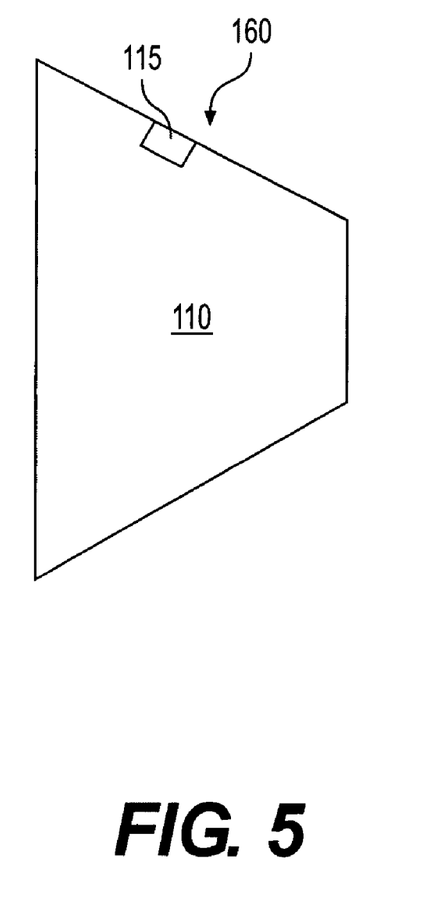
FIG. 5 illustrates an exemplary cross-sheet used in the exemplary oven intake of FIG. 1 to improve airflow speed.

FIG. 5 illustrates an exemplary cross-sheet 110 used in the exemplary oven intake 100 to improve airflow speed. The metal tabs 115 are riveted to secure the cross-sheets 110 to the intake duct wall. Other methods of securing, for example, screws, bolts, etc., may be used. The cross-sheets 110 shown in FIG. 5 has a converging shape 160 that conforms to and approximates the intake duct's convergent geometry 165.

Figure 6:
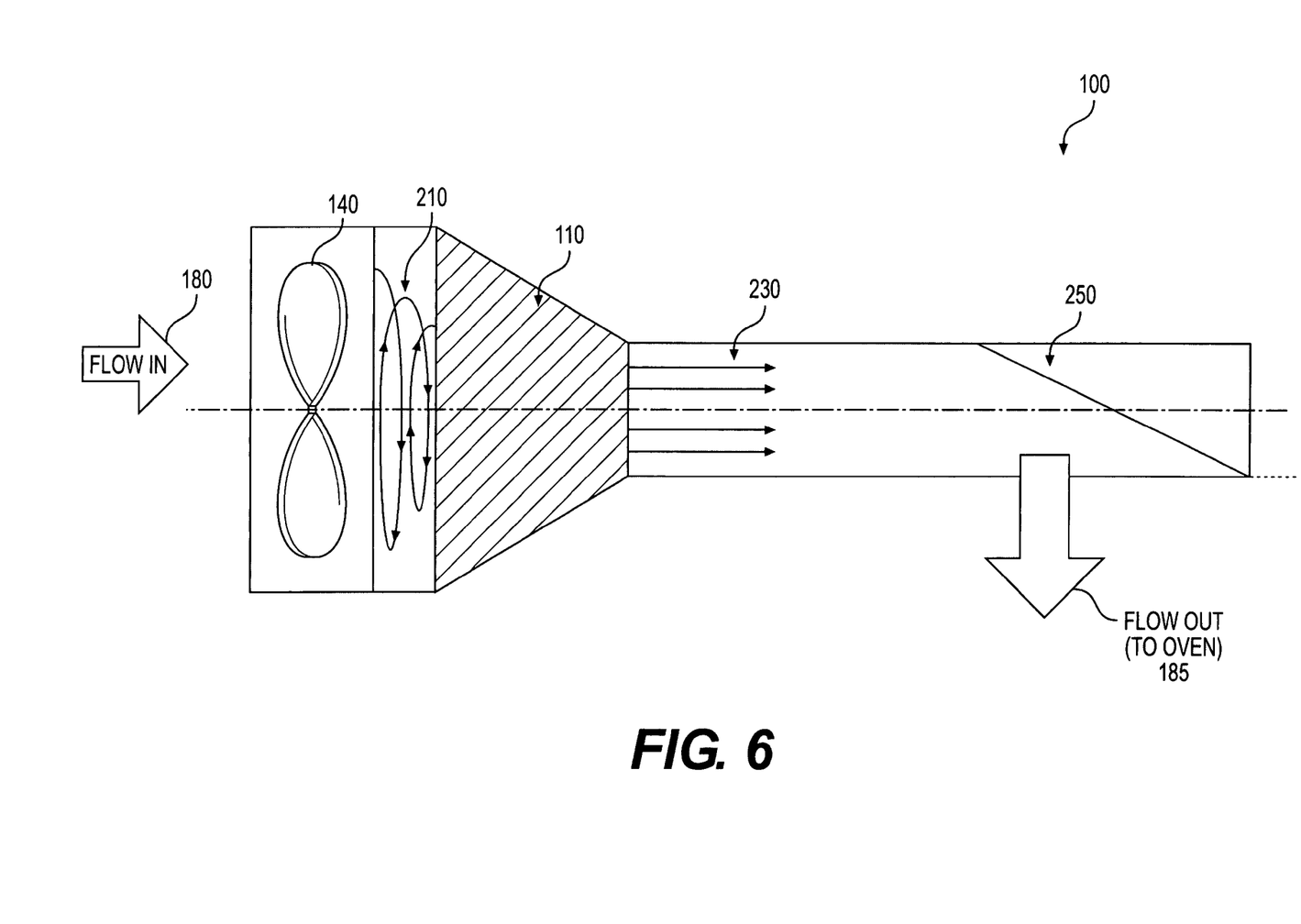
FIG. 6 illustrates a cutaway side view of the exemplary oven intake of FIG. 1 showing the direction of airflow into a GC oven.

FIG. 6 illustrates a cutaway side view of the exemplary oven intake 100 showing the direction 185 of airflow into the GC oven. As stated above, the intake fan 140 supplies airflow in the direction 180. The airflow is guided 230 by the cross-sheets 110 located inside the intake duct 120 directly in front of the intake fan 140. The guided airflow flows through the converging intake duct 120 into the GC oven in the direction 185. The utilization of the cross-sheets 110 reduces the airflow spin 210 induced by the intake fan 140 and sustained by the convergent geometry 165 of the intake duct 120, increasing the flow rate and volume of fresh air into the GC oven.

The overall cool-down time of the GC oven may be reduced as the flow rate of fresh air into the GC oven is increased. Also, the noise in the temperature signal may be reduced because the improved airflow allows the oven wall temperature to quickly match the oven air temperature. As a result, the GC oven can reach an equilibrium "ready" state faster. In addition, the utilization of the cross-sheets 110 may allow for flexibility in the design of a fast GC oven without loss of performance. For example, converging intake ducts may be used to allow larger intake fans located remotely from a small oven to be used during cool-down without suffering frictional losses induced by the airflow spin 210.

The following experiments illustrate the benefit of using the cross-sheet 110, specifically measured as the flow rate of air exhausted from the GC oven into open air.

One type of experiment is a battery of airflow measurements. In this experiment, an oven without insulation or support, such as an Agilent 6850 inner oven, is equipped with an axial fan 140 and one or more cross-sheets 110. The cross-sheets are placed in various locations in the oven intake duct 120. The oven stirring fan is not present in this experiment. The oven is sealed with a plastic cover.

The flow rate of air exhausted from the oven is measured using both a vane anemometer and a hot-wire anemometer. An anemometer is an instrument for measuring and indicating airspeed. Because the airspeed varies over the cross-section of the oven's exhaust duct (not shown), four points are taken to generate an average velocity. The experiment is performed at room temperature and under standard pressure. Table 1 illustrates the results of this experiment.

TABLE 1

| Number of Cross-Sheets | Airspeed (m/s) Vane Anemometer | Airspeed (m/s) Hot-wire Anemometer |
|---|---|---|
| 0 | 3.300 | 3.1725 |
| 1 | 3.475 | N/A |
| 2 | 3.650 | 3.450 |
| 3 | 3.675 | 3.425 |

Although some discrepancy exists over absolute values between the vane anemometer and the hot-wire anemometer, the trend is evident. The airspeed increases with the presence of the cross-sheets 110. For this particular application little if any improvement is shown when using more than two cross-sheets 110. As a result, the preferred number of cross-sheets is two.

For the special case of one cross-sheet, the cross-sheet is off-centered, for example, at one-third of the width of the intake duct, to generate the beneficial result illustrated in Table 1. If the cross-sheet is centered along the width of the intake duct, the cooling time actually increases.

A second type of experiment is more application specific. This experiment compares the cooling profile of GC ovens, such as Agilent 6850GC prototype ovens, that are equipped with one or more cross-sheets 110 with the same GC ovens without the cross-sheets 110. Table 2 illustrates the cool-down time of an Agilent prototype oven, which is geometrically similar to a standard Agilent 6850GC oven with the exception of the wall material. In addition, a more efficient intake fan 140 is used in this experiment, and the observed benefit of two cross-sheets 110 is apparent as shown below in Table 2.

TABLE 2

| Prototype Oven with More Efficient Fan | |
|---|---|
| Cross-sheets? | Cool-down Time (min) |
| No | 4.07 |
| Yes | 3.40 |

As shown in this experiment, the addition of two cross-sheets 110 inside the intake duct 120 reduces the cool-down time of the GC oven by more than 16%.

While the system and method for providing intake cross-sheets for a GC oven have been described in connection with an exemplary embodiment, those skilled in the art will understand that many modifications in light of these teachings are possible, and this application is intended to cover variations thereof.

What is claimed is:

1. An oven intake for a gas chromatographic (GC) oven, comprising:
   an intake duct having a convergent geometry to accommodate a small oven, the intake duct having one or more intake fans that supply airflow to the GC oven, wherein the airflow originates from the one or more intake fans and flows through the intake duct into the GC oven; and
   one or more cross-sheets positioned inside the intake duct parallel to a direction of the airflow flowing into the GC oven, wherein the one or more cross-sheets reduce spin of the airflow originating from the one or more intake fans and help guide the airflow through the intake duct into the GC oven.

2. The oven intake of claim 1, wherein the intake duct has a non-uniform cross-section.

3. The oven intake of claim 1, wherein each of the one or more cross-sheets has a converging shape that conforms to the convergent geometry of the intake duct.

4. The oven intake of claim 1, wherein each of the one or more cross-sheets is secured to the intake duct by riveting one or more metal tabs.

5. The oven intake of claim 1, wherein the number of cross-sheets positioned inside the intake duct to guide the airflow through the intake duct is one of: two, three or four.

6. The oven intake of claim 1, wherein one cross-sheet is installed off center with respect to an axis of spin of the airflow to guide the airflow through the intake duct.

7. The oven intake of claim 1, wherein the one or more cross-sheets are positioned proximately to the one or more intake fans inside the intake duct.

8. The oven intake of claim 1, wherein the one or more intake fans are axial boxer fans located at one end of the intake duct.

9. The oven intake of claim 1, wherein the intake duct has a conical shape.

10. The oven intake of claim 1, wherein the one or more cross-sheets reduce frictional losses of the airflow flowing into the GC oven, introduce a larger volume of air to the GC oven, and reduce a cool-down time of the GC oven.

11. The oven intake of claim 1, wherein two cross-sheets are placed in an "=" configuration at one-third and two-thirds of a width of the intake duct.

12. The oven intake of claim 1, wherein the spin of the airflow originates from a source other than the one or more intake fans.

13. A system for providing intake cross-sheets for a gas chromatographic (GC) oven, comprising:
    an intake duct having a convergent section to accommodate the GC oven located at one end of the intake duct;
    one or more intake fans located remotely from the GC oven at an opposite end of the intake duct, the one or more intake fans supplying airflow to the GC oven; and
    one or more cross-sheets positioned inside the intake duct parallel to a direction of the airflow flowing into the GC oven, wherein me one or more cross-sheets reduce spin of the airflow originating from the one or more intake fans and reduce frictional losses of the airflow flowing into the GC oven.

14. The system of claim 13, wherein each of the one or more cross-sheets has a converging shape that approximates the convergent section of the intake duct.

15. The system of claim 13, wherein two cross-sheets are positioned inside the intake duct to guide the airflow through the intake duct.

16. The system of claim 13, where the one or more cross-sheets are positioned proximately to the one or more intake fans inside the intake duct.

17. A method for cooling an oven, comprising:
    providing one or more cross-sheets inside an intake duct parallel to a direction of airflow flowing into the oven, wherein the intake duct has a convergent geometry to accommodate the oven and has one or more intake fans located remotely from the oven, and wherein the one or more intake fans supply airflow for the oven; and
    enabling the one or more cross-sheets to reduce spin of the airflow originating from the one or more intake fans and reduce a cool-down time of the oven, wherein each of the one or more cross-sheets has a converging shape that conforms to the convergent geometry of the intake duct.

18. The method of claim 17, further comprising positioning two cross-sheets inside the intake duct to help guide the airflow through the intake duct.

19. The method of claim 17, further comprising positioning the one or more cross sheets proximately to the one or more intake fans inside the intake duct.

* * * * *

UNITED STATES PATENT AND TRADEMARK OFFICE
CERTIFICATE OF CORRECTION

PATENT NO.     : 6,920,777 B1
DATED          : July 26, 2005
INVENTOR(S)    : Miller It is certified that error appears in the above-identified patent and that said Letters Patent is hereby corrected as shown below:

Column 6,
Line 45, delete "me" and insert -- the --, therefor.

Column 8,
Line 2, delete "cross sheets" and insert -- cross-sheets --, therefor.

Signed and Sealed this

Twenty-second Day of November, 2005

JON W. DUDAS
*Director of the United States Patent and Trademark Office*